United States Patent [19]

Hunter et al.

[11] Patent Number: 4,954,449

[45] Date of Patent: Sep. 4, 1990

[54] HUMAN MONOCLONAL ANTIBODY REACTIVE WITH POLYRIBOSYLRIBITOL PHOSPHATE

[75] Inventors: Kenneth W. Hunter, Kensington; Gerald W. Fischer, Gaithersburg, both of Md.

[73] Assignee: The United States of America as represented by the Secretary of the Army, Washington, D.C.

[21] Appl. No.: 155,437

[22] Filed: Feb. 12, 1988

Related U.S. Application Data

[62] Division of Ser. No. 411,115, Aug. 24, 1982, Pat. No. 4,744,982.

[51] Int. Cl.$^5$ .................... C12N 5/00; C07K 15/00; C07K 15/28
[52] U.S. Cl. .................... 435/240.27; 530/387; 424/85.8; 424/87
[58] Field of Search .............. 435/240.27, 172.2, 85.8, 435/87; 530/387

[56] References Cited

U.S. PATENT DOCUMENTS 4,220,717  9/1980  Kuo ........................................ 424/92
4,407,949  10/1983  Kniskern et al. ...................... 424/92

Primary Examiner—Blondel Hazel
Attorney, Agent, or Firm—Werten F. W. Bellamy

[57] ABSTRACT

A human monoclonal antibody produced by a self-reproducing carrier cell, the antibody being reactive with PRP capsular polysaccharide. Also disclosed is a process of preparing the antibody from the carrier cell, which is conveniently a hybridoma. Additionally, diagnostic, prophylactic and therapeutic compositions and methods employing the antibody are disclosed. Moreover, a laboratory reagent containing the antibody is described.

2 Claims, No Drawings

HUMAN MONOCLONAL ANTIBODY REACTIVE WITH POLYRIBOSYLRIBITOL PHOSPHATE

U.S. GOVERNMENT RIGHTS

The invention described herein may be manufactured, used and licensed by or for the U.S. Government for governmental purposes without the payment to us of any royalties thereon.

This is a division of application Ser. No. 411,115, filed Aug. 24, 1982 now Pat. No. 4,744,982.

TECHNICAL FIELD

This invention relates to a novel self-reproducing carrier cell and more specifically to a carrier cell containing genes for the production of human monoclonal antibody reactive with antigenic polyribosylribitol phosphate capsular polysaccharide, to the antibody, to a process of preparing the antibody from the carrier cell, to diagnostic, prophylactic and therapeutic methods and compositions employing this antibody, and to a research composition employing this antibody.

BACKGROUND ART

*H. influenzae* type b is an important cause of disease, particularly in infants and small children who fail to produce antibodies following active immunization. See J. C. Parke, Jr. et al, *J. Pediatr.*, 81:765 (1972); J. Ward et al, *N. Eng. J. Med.*, 301:122 (1979); and H. Petola et al, *Pediatrics*, 60:730 (1977). The rapid diagnosis of *H. influenzae* type b disease is important for the selection and timely administration of antibiotics. The *H. influenzae* type b bacterium is particularly characterized by a polyribosylribitol phosphate (PRP) capsular polysaccharide. Another pathogenic microorganism bearing PRP capsular polysaccharide is *E. coli* having the K100 antigen. This pathogen is known to produce septicemia, pneumonia and meningitis in humans. Other pathogens bearing PRP capsular polysaccharide may yet be identified. The pathogenicity of the two known PRP-bearing microorganisms is believed to be limited primarily to humans.

Currently, polyclonal anti-PRP antibodies raised in animals such as rabbits are employed in various assays to identify the PRP antigen. However, such polyclonal reagents often have more than one specificity and therefore tend to produce unwanted cross reactions. PRP isolated from *H. influenzae* type b bacterium has also been used to prepare a combined vaccine, as exemplified in U.S. Pat. No. 4,220,717 to Kuo. Also known is an assay for the detection of PRP capsular polysaccharide, as exemplified by U.S. Pat. No. 4,310,508 to Siber.

The technique of fusing cells to produce viable hybrids that express characteristics of both parental cells has been known for a number of years. In *Nature*, 256:495 (1975), Köhler and Milstein reported the successful fusion of mouse B lymphocytes and mouse plasmacytoma cells to form hybrids that secreted monoclonal antibodies of predefined specificity. In *Proc. Nat'l. Acad. Sci., USA*, 77:5429 (1980), Olsson and Kaplan documented the first human-human hybridomas that secreted human monoclonal antibodies. In order to avoid the cross reactions of polyclonal anti-PRP antibodies, to provide a very precise antibody for the rapid diagnosis of disease caused by a PRP-bearing pathogen, and to provide an endless supply of antibody that can be generated in vitro, there is needed a self-reproducing carrier cell containing genes that produce a human monoclonal anti-PRP antibody and a method for producing the antibody from the carrier cell. Such an antibody would be, to our knowledge, the first human monoclonal antibody reactive with a major human pathogen. Advantageously, this antibody could be produced by in vitro culturing of the carrier cell, thereby avoiding injection of the antigen into an animal and later killing the animal.

As a result of the inability to vaccinate certain high risk groups such as infants and immunosuppressed adults, there is also a need for a means of passive prophylaxis against disease caused by a PRP-bearing pathogen, using a human monoclonal antibody. Additionally, a human monoclonal antibody that is therapeutically effective against an existing disease caused by a PRP-bearing pathogen would be of substantial value. Such an antibody would be, to our knowledge, the first human monoclonal antibody to demonstrate a functional activity against a pathogenic organism.

Moreover, there is a need for a laboratory reagent for dissecting the chemical structure of PRP capsular polysaccharide.

DISCLOSURE OF THE INVENTION

It is accordingly one object of the present invention to provide a self-reproducing carrier cell containing genes that produce a human monoclonal antibody reactive with PRP capsular polysaccharide.

It is a further object to provide the antibody so produced.

A still further object is to provide a method of preparing the antibody from the carrier cell.

An even further object is to provide methods and compositions for diagnosis, prophylaxis and treatment of PRP-bearing pathogen-caused disease, that employ this antibody.

Another object is to provide a laboratory reagent containing the antibody that is useful for research into the chemical structure of PRP.

Other objects and advantages of the present invention will become apparent as the description thereof proceeds.

In satisfaction of the foregoing objects and objectives, there is provided by this invention a human monoclonal antibody reactive with antigenic PRP capsular polysaccharide. The antibody is produced by a self-reproducing carrier cell containing genes that produce a human monoclonal antibody reactive with antigenic PRP capsular polysaccharide. Also provided by the invention is the carrier cell, which conveniently is a cell line such as a hybridoma. Additionally, there is provided in satisfaction of the foregoing objects and objectives, a process of preparing the antibody. This process includes culturing the carrier cell in a suitable medium for an appropriate period of time, and recovering the antibody from the supernatant above the carrier cell.

Also provided by this invention is an immunodiagnostic method for the diagnosis in a human of an infection caused by a pathogenic microorganism bearing an antigenic PRP capsular polysaccharide. This method includes mixing a diagnostically effective amount of the antibody of this invention with a sample of a body fluid removed from the human, and measuring the degree of reaction in the resulting mixture.

The present invention also provides a diagnostic composition for the diagnosis of an infection caused by a pathogenic microorganism bearing an antigenic PRP capsular polysaccharide. This composition includes, in admixture with a diagnostically acceptable carrier, a concentration of the antibody effective to diagnose the infection.

Also provided by the present invention in satisfaction of the foregoing objects and objectives is an immunoprophylactic method for passive prophylaxis of a human against an infection caused by a pathogenic microorganism bearing an antigenic PRP capsular polysaccharide. This method includes injecting the human, prior to the human having an infection caused by the microorganism, with an amount of the antibody effective to result in passive prophylaxis.

Also provided is a composition for passive prophylaxis against such an infection, the composition including, in admixture with a physiologically acceptable carrier, a concentration of the antibody effective to result in passive prophylaxis.

Also in satisfaction of the foregoing objects and objectives, there is provided by this invention an immunotherapeutic method for therapeutically treating a human having an infection caused by a pathogenic microorganism bearing an antigenic PRP capsular polysaccharide. This method includes injecting the human with an amount of the antibody effective to result in amelioration of the infection. Also provided is a composition for therapeutic treatment of such an infection, the composition including, in admixture with a physiologically acceptable carrier, a concentration of the antibody of the present invention effective to result in amelioration of the infection.

Finally, there is provided by this invention a composition useful for research into the chemical structure of PRP capsular polysaccharide. This composition includes, in admixture with a carrier suitable for research, an amount of the antibody of the present invention effective to provide information as to the chemical structure upon being mixed with PRP, degradation of the resulting reaction product, and analysis.

The preparation and characterization of the self-reproducing carrier cell and the resultant antibody will be better understood by reference to the following description.

BEST MODE FOR CARRYING OUT THE INVENTION

As indicated, the scope of the present invention embraces any self-reproducing carrier cell containing genes that produce a human monoclonal antibody reactive with antigenic PRP capsular polysaccharide. This carrier cell is principally characterized not only by being self-reproducible but also by having the genes that produce the antibody. Conveniently, the carrier cell is a hybridoma, and for purposes of illustrating the invention, the following discussion is primarily in terms of a hybridoma. However, the present invention includes antibody-producing genes cloned into a microorganism or genes residing in the parental lymphoid cell that has been transformed by, for example, Ebsen-Barr virus. Thus, the carrier cell could be a microorganism such as $E.\ coli$.

In making a hybridoma in accordance with the invention, splenic tissue containing human lymphoid cells was obtained with informed consent from an 11 year old white female splenectomized following a 2 year history of idiopathic thrombocytopenic purpura unresponsive to prednisone. Other sources of human lymphoid cells that could have been used include lymph nodes, tonsils and peripheral blood.

The patient was not given PRP vaccine prior to surgery, and her clinical history did not reveal a previous overt episode of $H.\ influenzae$ type b infection. However, one would expect immunologic experience with respect to $H.\ influenzae$ type b by about the age of 5 or 6.

The splenic tissue was dissociated into a single cell suspension in tissue culture medium and cryopreserved using a rate-controlled liquid nitrogen freezer. Aliquots of the cryopreserved cells were stored at $-179°$ C. in liquid nitrogen vapor phase.

An appropriate human myeloma fusion partner was selected. In this case, the partner was HFB-1 (human fusion B cell-1), a mutant tumor line deficient in the enzyme hypoxanthine-guanine phosphoribosyl transferase (HGPRT-). This cell line was donated by Robert J. Hartzman, M.D., of Georgetown University School of Medicine.

The splenic lymphocytes were thawed, hybridomas were prepared and purified anti-PRP was obtained using routine procedures. The splenic lymphocytes were fused with HFB-1 in the presence of a suitable fusion promoter, which in this case was 50% polyethylene glycol (MW, 1400), generally according to the now standard technique of Olsson and Kaplan described in *Proc. Nat'l. Acad. Sci., USA*, 77:5429 (1980), which is hereby incorporated by reference into this description. The early hybrids were grown in accordance with a customary procedure in microcultures in hypoxanthine-aminopterin-thymidine medium, which kills all HGPRT- parental myelomas. After 14 days of culture, the supernatants of the microcultures were screened by enzyme immunoassay for the presence of antibodies that bind to PRP capsular polysaccharide of the bacterium *Haemophilus influenzae* type b. A positive culture was cloned by limiting dilution on a feeder cell, which in this case was irradiated mouse tumor macrophages (P388D1). After 19 days, the microcultures were retested by enzyme immunoassay to identify clones that secreted monoclonal anti-PRP antibody. One clone designated C3,H12 by us was selected and grown in large-scale culture. By Ouchterlony analysis, the antibodies of this clone were determined to be of the IgG isotype, and by using Protein A Sepharose affinity chromatography, purified IgG anti-PRP antibody was obtained. The subclass of this antibody appears to be IgG1. As indicated earlier, now that we have described the procedures for obtaining this carrier cell, we believe that a person skilled in this art will be able to reproduce our work and obtain a self-reproducing carrier cell containing genes that produce human monoclonal antibody reactive with antigenic polyribosylribitol phosphate capsular polysaccharide.

To assess the specificity, the purified anti-PRP antibody was tested according to the standard in vitro neutrophil-mediated opsonophagocytic assay of G. W. Fischer, G. H. Lowell, M. H. Crumrine, and J. W. Bass in *J. Exp. Med.*, 148:176 (1978), which is hereby incorporated by reference into this description.

In carrying out this microtiter plate assay, we placed in each well of the microtiter plate a standard mixture of $5.0 \times 10^6$ colony forming units (CFU) of $H.\ influenzae$ type b, $1.0 \times 10^6$ neutrophils from human peripheral blood, 10% normal rabbit complement (prescreened for lack of bactericidal activity), and Eagle's minimal essential medium. To each of three wells, a selected concentration of the human monoclonal anti-PRP was added. Samples were removed from the resulting reaction mixture at 0, 60 and 120 min.

The possibility that the results obtained were due to agglutination prior to dilution and plating was excluded in two separate experiments by placing the total contents of each well on chocolate agar after 120 minutes incubation. A significant reduction in total bacterial growth was observed.

An inhibition experiment was performed by preincubating 100 μg PRP with 100 μg of the human monoclonal anti-PRP for 30 minutes at 4° C. and then transferring an appropriate amount of the resulting mixture that contained 20 μg of the anti-PRP to a well containing the standard mixture. Samples were again removed at 0, 60 and 120 minutes. This inhibition experiment was repeated except that 100 μg Type XIV pneumococcal antigen (P14) was substituted for the PRP.

To another well containing the standard mixture, human monoclonal IgG antibody (anti-Pn) without PRP binding activity (demonstrated by enzyme immunoassay) was added. Samples were once again removed at 0 and 120 minutes. Finally, the human monoclonal anti-PRP was tested for antibacterial activity against Group B Streptococcus (GBS), strain IIINor.

Controls with complement only, neutrophils only, or complement plus neutrophils invariably demonstrated no antibacterial activity.

The results of this assay are shown in the following Table.

| Antibody | μg[1] | CFU × 10$^6$ 0 min | 60 min | 120 min | % Killing 120 min |
|---|---|---|---|---|---|
| anti-PRP | 20 | 5.7 | 0.8 | 0 | 100 |
| anti-PRP | 10 | 5.4 | 1.5 | 0.5 | 91 |
| anti-PRP | 5 | 6.7 | 4.4 | 4.0 | 40 |
| anti-PRP + PRP | 20 | 4.8 | 5.5 | 6.5 | 0 |
| anti-PRP + P14 | 20 | 5.7 | 1.2 | 0.1 | 99 |
| anti-Pn | 20 | 6.1 | ND[2] | >10.0 | 0 |
| anti-PRP against GBS,IIINor | 20 | 5.0 | ND[2] | 5.6 | 0 |

[1] Expressed as μg/100 μl total reaction mixture
[2] Not done

As demonstrated in the Table, as little as 10 μg of the anti-PRP antibody significantly inhibited the growth of *H. influenzae* type b. This growth inhibitory activity demonstrates that the antibody may be of therapeutic value.

Still referring to the Table, a concentration of 100 μg of purified PRP blocked the growth inhibitory activity of the anti-PRP antibody, whereas a similar concentration of pneumococcal type XIV capsular polysaccharide (P14) failed to block the inhibitory activity. The anti-PRP antibody had no effect on the in vitro growth of Type III Group B Streptococcus (strain IIINor). These data point to the specificity of the C3,H12 antibody for PRP and demonstrate its usefulness as a diagnostic reagent.

The human monoclonal antibody of this invention is a very specific reagent that can be used to identify PRP antigen in body fluids, and thus diagnose cases of disease caused by a pathogenic microorganism bearing PRP capsular polysaccharide. This antibody has a distinct advantage over currently used polyclonal reagents in its lack of cross reactivity with other bacterial and human antigens. Additionally, this antibody may be useful as a means of passive prophylaxis, possibly working in concert with human neutrophils, and may be useful for therapeutic treatment. Usefulness of the antibody is discussed herein primarily in terms of diagnosis, prophylaxis and therapeutic treatment in humans. However, veterinary usefulness could exist if a PRP-bearing microorganism is found to be a pathogen of substantial importance in domesticated animals.

The antibody can be packaged and sold in freeze-dried form for subsequent use diagnostically, prophylactically, therapeutically, or for research purposes. However, it is also possible to admix the antibody with an appropriate carrier. An appropriate carrier for forming a diagnostic composition, a composition for passive prophylaxis or a therapeutic composition is a balanced aqueous salt solution, and an appropriate carrier for a laboratory reagent containing the antibody is purified water.

A diagnostic composition in accordance with the present invention contains a concentration of the antibody effective to diagnose the infection, a composition for passive prophylaxis in accordance with the present invention contains a concentration of the antibody effective to result in passive prophylaxis, and a composition for therapeutic treatment in accordance with the present invention contains a concentration of the antibody effective to result in amelioration of the infection. These concentrations are readily determinable, and are dependent upon factors including those discussed below. A laboratory composition, in accordance with the present invention, useful for research into the chemical structure of PRP capsular polysaccharide, contains an amount of the antibody effective to provide information as to the chemical structure upon being mixed with PRP, degradation of the resultant reaction product, and analysis. Determination of this amount is also readily within the skill of one carrying out this type of research work. The specificity for PRP exhibited by the antibody should allow a more precise dissection of the antigenic structure of this capsular polysaccharide.

In an immunodiagnostic method, in accordance with this invention, the antibody of the present invention is mixed with a sample of a body fluid removed from a human who may have an infection caused by a PRP-bearing pathogenic microorganism, and the degree of reaction in the resulting mixture is then measured. The body fluid may, for example, be spinal fluid. The amount of the antibody needed for carrying out the diagnosis depends upon factors that include the amount of the sample to be tested. Thus, a relatively greater amount of the antibody is needed for a relatively larger sample, whereas a relatively smaller amount is needed for a relatively smaller sample.

When used for passive prophylaxis of a human against an infection caused by a PRP-bearing pathogenic microorganism, the antibody will be injected into the human prior to the human having an infection caused by the microorganism. The amount of the antibody injected will depend upon factors that include the weight of the human. The human typically will be an infant or an immunosuppressed adult.

When the antibody of the present invention is used for therapeutic treatment of a human having an infection caused by a PRP-bearing pathogenic microorganism, the antibody will be administered by injection. The amount of the antibody needed to result in amelioration of the infection will depend upon factors including the weight of the individual being treated, as well as the severity of the infection.

In preparing the antibody from the hybridoma, the hybridoma may be cultured in most standard tissue culture mediums. A particularly useful medium is RPMI 1640, available from MA Bioproducts of Walkersville, Md. The time appropriate for the culturing depends upon factors that include the quantity of hybridoma to be cultured and the quantity of antibody that is desired. Depending on the quantity of hybridoma that is cultured, about one milligram of the antibody can be produced in about one week using RPMI 1640. When the time for culturing is complete, the antibody is recovered from the supernatant using conventional techniques.

When the carrier cell is a microorganism, antibody production is accelerated since a microorganism such as *E. coli* replicates in about 20 minutes, whereas the hybridoma replicates in about 24 hours. Antibody production from the microorganism or transformed parental lymphoid cell is essentially carried out in about the same manner as described above, with an appropriate culture medium being used. In vitro production from a carrier cell in accordance with the invention results in a highly pure antibody. The carrier cell is used in a pure culture form.

It is possible that a multitude of human monoclonal antibodies all reactive with PRP but of different isotypes and with different molecular specificities or affinities, may be produced in the future. An important feature of any such antibodies, for purposes of this invention, is reactivity with PRP capsular polysaccharide. Thus, this invention includes any human monoclonal antibody that reacts with PRP capsular polysaccharide, regardless of isotype, molecular specificity, or affinity, the antibody being produced by a self-reproducing carrier cell.

Furthermore, since, for purposes of this invention, the human monoclonal antibody-producing genes of the hybridoma are a key part of the hybridoma, this invention includes a human monoclonal antibody produced by these genes cloned into a microorganism.

Similarly, it is possible that a number of self-reproducing carrier cells all producing human monoclonal antibody of the type described herein could be made. Since a feature of any such carrier cells that is important, for purposes of this invention, is production of the antibody described in this description, the scope of this invention embraces any self-reproducing carrier cell that produces this antibody.

APPLICABILITY

This invention is useful for the diagnosis of PRP-bearing pathogenic microorganism-caused disease, such as *H. influenzae* type b. Additionally, the antibody of this invention may be useful for passive prophylaxis and therapeutic treatment of this type of disease. Also, this antibody is useful for research into the chemical structure of PRP capsular polysaccharide.

We claim:

1. A self-reproducing hybridoma containing genes that produce a human monoclonal antibody reactive with antigenic polyribosybribitol phosphate capsular polysaccharide.

2. A human monoclonal antibody reactive with and providing effective passive prophylaxis or therapy against infection caused by pathogenic bacteria bearing antigenic capsular polysaccharides, said antibody produced by the hybridoma of claim 1 containing genes that produce a protective human antibody.

* * * * *